(12) United States Patent
Johnson

(10) Patent No.: US 6,572,655 B1
(45) Date of Patent: Jun. 3, 2003

(54) METHOD FOR SECURING A PROSTHESIS COMPONENT TO BONE

(76) Inventor: Lanny L. Johnson, 3800 Hagadom Rd., Okomoe, MI (US) 48864

( * ) Notice: Subject to any disclaimer, the term of this patent is extended or adjusted under 35 U.S.C. 154(b) by 274 days.

(21) Appl. No.: 09/684,838

(22) Filed: Oct. 10, 2000

Related U.S. Application Data

(63) Continuation-in-part of application No. 09/140,421, filed on Aug. 26, 1998, now abandoned.

(51) Int. Cl.[7] .................................................. A61F 2/32
(52) U.S. Cl. ...................... 623/22.36; 606/73
(58) Field of Search ............... 623/20.14, 39, 623/16.11, 17.11, 923, 20.17, 18.11, 19.11, 20.11, 21.11, 908, 19.12, 20.21, 22.11, 22.21, 22.36; 606/61, 65, 72, 73, 76

(56) References Cited

U.S. PATENT DOCUMENTS 4,484,570 A * 11/1984 Sutter et al.
5,209,753 A 5/1993 Biedermann et al.
5,246,441 A 9/1993 Ross et al.
5,334,204 A 8/1994 Clewett et al.
5,360,452 A * 11/1994 Engelhardt et al. ...... 623/18.11
5,718,706 A * 2/1998 Roger .......................... 606/73
5,735,898 A * 4/1998 Branemark ............... 623/16.11
5,968,047 A * 10/1999 Reed ........................... 606/76
5,984,966 A 11/1999 Kiema et al.
6,102,951 A * 8/2000 Sutter et al. ............. 623/18.11

OTHER PUBLICATIONS

A. Weiler et al., "Hamstring Tendon Fixation Using Interference Screws: A Biomechanical Study in Calf Tibial Bone," Arthroscopy: Journal of Arthroscopic and Related Surgery, vol. 14, No. 1 (Jan.–Feb.), 1998: pp. 29–36.

* cited by examiner

*Primary Examiner*—Todd E. Manahan

(57) ABSTRACT

A biodegradable screw is used to secure a prosthesis component to bone, the screw disclosed having a head portion, a threaded portion, and a bore extending along the screw's longitudinal axis through the head portion and through at least a substantial length of the threaded portion.

12 Claims, 1 Drawing Sheet

METHOD FOR SECURING A PROSTHESIS COMPONENT TO BONE

The present application is a continuation-in-part of U.S. application Ser. No. 09/140,421, filed on Aug. 26, 1998 now abandon.

BACKGROUND OF THE INVENTION

1. Field of the Invention

The present invention relates to a biodegradable screw used to secure a prosthesis component to bone. The invention is particularly suited to joining an acetabular cup to the acetabulum.

2. Prior Art

The use of screws made of a biodegradable material in surgical procedures is known. For example, biodegradable interference screws heretofore have been employed in fixing grafts to bone. The purpose of using an interference screw formed from biodegradable material is to permit an initial physical joinder of the graft to the bone. However, as the screw degrades, the screw is replaced by bone growth whereby the attachment of the graft to the bone is achieved from the biological process of bone growth which holds the graft in place.

SUMMARY OF THE INVENTION

The present invention is a method for securing a prosthesis component to bone using a biodegradable screw comprising head and threaded portions. A bore is provided along the longitudinal axis of the screw extending entirely through the head portion and along at least a substantial length of the threaded portion. The bore is adapted to receive harvested bone within the screw. Additionally, in the head portion, the bore is configured to receive a screw driving component, such an allen wrench, which permits the screw to be implanted within a bore formed in bone. With a screw so implanted and the bore containing harvested bone, the degradation of the screw results in improved and accelerated bone growth in replacement for the screw.

DETAILED DESCRIPTION OF THE DRAWINGS

The invention will be described in greater detail with respect to the accompanying drawings, wherein.

DETAILED DESCRIPTION OF PREFERRED EMBODIMENTS OF THE INVENTION

Figure 1:
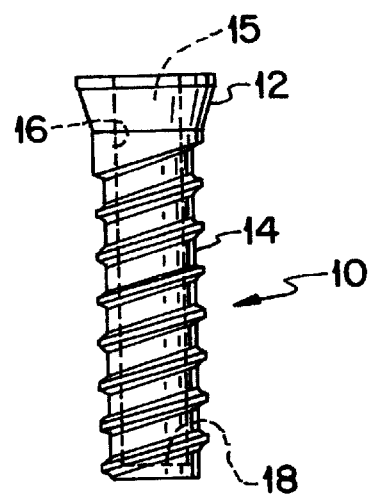
FIG. 1 is a side elevational view of a biodegradable screw used according to the invention.
Figure 2:
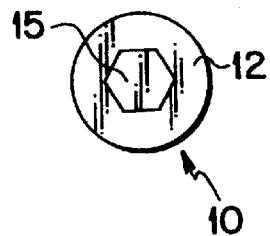
FIG. 2 is a top plan view thereof.

Referring to FIGS. 1 and 2, a screw 10 is illustrated comprising a head portion 12 and a threaded portion 14. The screw is formed from a biodegradable material, such as 85/15 D,L lactide/glycolide. It is provided with a bore 15 extending through head portion 12 and along the longitudinal axis of the screw substantially the entire length of the threaded portion 14. Thus, the threaded portion has a sidewall 16 and a bottom wall 18.

The head portion 12 is configured to receive a driver so that the screw can be inserted within a cavity provided in a bone. Once this occurs, the bore 15 is filled with bone which has been harvested during the surgical procedure. As the screw deteriorates over time, the bone within bore 15 grows and migrates towards the bone growing outside the screw. As the sidewall 16, bottom wall 18 and head portion 12 continue to deteriorate, the bone growing within the screw fuses with that growing from outside the screw whereby the screw is replaced by bone growth.

As an alternative to the embodiment just described, the bore 15 passes completely through the screw 10 and is completely filled with harvested bone.

Figure 3:
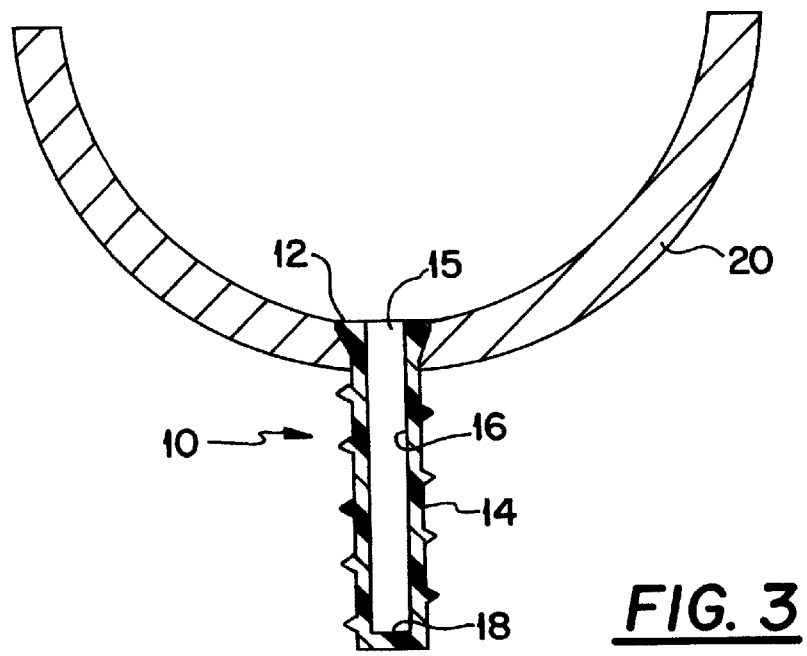
FIG. 3 is a cross-sectional view of a biodegradable screw used in securing an acetabular cup to bone.

The invention is particularly useful in securing an acetabular cup to the acetabulum. Referring to FIG. 3, a cup 20 is shown in cross-section. For purposes of illustration, only one screw 10 is shown. It will be understood, of course, that the cup is secured to the acetabulum by several screws.

An acetabular cup typically includes a plastic insert (not shown) covering the cup's concave surface to serve as a liner which receives the femoral head of a prosthesis. When the cup is secured by conventional screws, wear particles from the insert can move along the threaded exterior of the screws into the acetabulum resulting in osteolysis. However, when biodegradable screws are used, the bone growth which replaces the degraded screw prevents such movement of wear particles. Moreover, as the head portion of the screw shown in FIG. 3 is replaced by bone growth, such growth provides permanent fixation for cup 12 and serves as a barrier to materials passing through the screw holes in the cup.

Of course, screw 10 is dimensioned properly for each application, and may be tapered to facilitate insertion into a cavity prepared in the bone and to mate with a tapered screw hole in the acetabular cup.

What is claimed is:

1. A method for securing a prosthesis component to bone by inserting a biodegradable screw through an opening in the component into a cavity formed in the bone, said biodegradable screw comprising:

a head portion;

a threaded portion formed integrally with the head portion and extending into the cavity;

a bore formed in the screw, said bore extending through the head portion and within the threaded portion along a longitudinal axis of the screw for at least a substantial length of the threaded portion; and filling said bore with harvested bone.

2. A method according to claim 1, wherein said bore extends the entire length of the threaded portion.

3. A method according to claim 2, wherein said bore within the head portion is configured to receive a driver for the screw.

4. A method according to claim 3, wherein said biodegradable screw is formed from a D,L lactide material.

5. A method according to claim 4, wherein said material is 85/15 D,L lactide/glycolide.

6. A method according to claim 2, wherein said biodegradable screw is formed from a D,L lactide material.

7. A method according to claim 6, wherein said material is 85/15 D,L lactide/glycolide.

8. A method according to claim 1, wherein said bore within the head portion is configured to receive a driver for the screw.

9. A method according to claim 8, wherein said biodegradable screw is formed from a D,L lactide material.

10. A method according to claim 9, wherein said material is 85/15 D,L lactide/glycolide.

11. A method according to claim 1, wherein said biodegradable screw is formed from a D,L lactide material.

12. A method according to claim 11, wherein said material is 85/15 D,L lactide/glycolide.

* * * * *